US009516998B2

(12) United States Patent
Iwasaki

(10) Patent No.: US 9,516,998 B2
(45) Date of Patent: Dec. 13, 2016

(54) IMAGE PICKUP APPARATUS FOR ENDOSCOPE

(75) Inventor: Seiji Iwasaki, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/467,099

(22) Filed: May 9, 2012

(65) Prior Publication Data

US 2012/0220828 A1 Aug. 30, 2012

Related U.S. Application Data

(63) Continuation of application No. PCT/JP2011/075714, filed on Nov. 8, 2011.

(30) Foreign Application Priority Data

Nov. 9, 2010 (JP) ................................. 2010-251045

(51) Int. Cl.
*A61B 1/00* (2006.01)
*A61B 1/06* (2006.01)
(Continued)

(52) U.S. Cl.
CPC .......... *A61B 1/00188* (2013.01); *A61B 1/0051* (2013.01); *A61B 1/0058* (2013.01); *A61B 1/05* (2013.01)

(58) Field of Classification Search
CPC .................................................. A61B 1/0125
(Continued)

(56) References Cited

U.S. PATENT DOCUMENTS 4,993,149 A * 2/1991 Zilligen et al. .................. 29/859
5,531,664 A 7/1996 Adachi et al.
(Continued)

FOREIGN PATENT DOCUMENTS

CN 101238967 A 8/2008
CN 101461702 A 6/2009
(Continued)

OTHER PUBLICATIONS

European Search Report dated Jun. 11, 2013 from corresponding European Patent Application No. 11 83 9372.7.

*Primary Examiner* — Ryan Henderson
*Assistant Examiner* — Aaron B Fairchild
(74) *Attorney, Agent, or Firm* — Scully, Scott, Murphy & Presser, P.C.

(57) ABSTRACT

An image pickup apparatus for an endoscope includes: an image pickup device unit including an image pickup device; a lens unit including a moving lens; an actuator apparatus for an endoscope, the actuator apparatus including a first elastic member having an urging force that makes a moving lens frame be arranged at a first observation position, a second elastic member making the moving lens frame be arranged at a second observation position, and a shape memory alloy wire having a property of extending/contracting due to an applied current; a driving force transmitting wire arranged on a distal end side of the shape memory alloy wire; a pressing member, upon receipt of an elastic force from the second elastic member, pressing the moving lens frame to the second observation position; and a fixing portion that fixes the driving force transmitting wire and the shape memory alloy.

11 Claims, 8 Drawing Sheets

(51) Int. Cl.
*A61B 1/005* (2006.01)
*A61B 1/05* (2006.01)

(58) Field of Classification Search
USPC .. 600/129, 130, 167, 168, 151, 174; 348/65; 359/823
See application file for complete search history.

(56) References Cited

U.S. PATENT DOCUMENTS

| | | |
|---|---|---|
| 6,117,071 A | 9/2000 | Ito et al. |
| 2005/0038317 A1* | 2/2005 | Ratnakar ..................... 600/156 |
| 2007/0100209 A1 | 5/2007 | Takahashi |
| 2008/0194914 A1 | 8/2008 | Iwasaki |
| 2009/0185032 A1 | 7/2009 | Sakai et al. |
| 2009/0303619 A1 | 12/2009 | Iwasaki et al. |
| 2010/0268027 A1 | 10/2010 | Aono et al. |

FOREIGN PATENT DOCUMENTS

| | | |
|---|---|---|
| EP | 1 955 645 A1 | 8/2008 |
| EP | 2 072 001 A2 | 6/2009 |
| EP | 2 130 482 A1 | 12/2009 |
| EP | 2 324 754 A1 | 5/2011 |
| JP | 11-197096 | 7/1999 |
| JP | 2007-229155 | 9/2007 |
| JP | 2008-194178 | 8/2008 |
| JP | 2009-066222 | 4/2009 |
| JP | 2009-291364 | 12/2009 |
| JP | 2009-300761 | 12/2009 |
| JP | 2010-020104 | 1/2010 |
| JP | 2010-046424 | 3/2010 |
| WO | WO 2010/047396 A1 | 4/2010 |
| WO | WO 2010/113658 A1 | 10/2010 |

\* cited by examiner

IMAGE PICKUP APPARATUS FOR ENDOSCOPE

CROSS REFERENCE TO RELATED APPLICATION

This application is a continuation application of PCT/JP2011/075714 filed on Nov. 8, 2011 and claims benefit of Japanese Application No. 2010-251045 filed in Japan on Nov. 9, 2010, the entire contents of which are incorporated herein by this reference.

BACKGROUND OF THE INVENTION

1. Field of the Invention

The present invention relates an image pickup apparatus disposed at a distal end portion of an insertion portion of an endoscope, and specifically relates to an image pickup apparatus for an endoscope, the image pickup apparatus including an actuator apparatus for an endoscope, the actuator apparatus advancing and retracting a moving lens frame.

2. Description of the Related Art

Electronic endoscopes are used for observations or treatments, etc., of insides of living bodies or inspections or repairs, etc., of insides of industrial plant facilities. In endoscopic observations, it is demanded that optical characteristics, such as a focal depth, a formed image magnification and a view angle, for an observation target portion can be changed according to, e.g., a site to be observed or a purpose of the observation.

In recent years, image pickup apparatuses have been known which include an objective lens group in which one or more optical lenses included in the objective lens group can be moved in an optical axis direction, enabling adjustment or change of optical characteristics. For example, with an endoscope enabling normal observation and enlarged observation, a moving lens frame that can be moved in an optical axis direction, which is arranged in an objective lens group included in an image pickup apparatus, is moved to the distal end side or the proximal end side by means of a moving mechanism, providing a desired observation state.

The endoscopes are configured so as to, for example, enter a normal observation state when the moving lens frame is moved to the distal end side of the insertion portion of the respective endoscope and enter an enlarged observation state as the moving lens frame is moved to the proximal end side. Such endoscopes are in a maximally-enlarged observation state when the moving lens frame has been moved to the furthest on the proximal end side. It should be noted that an amount of movement of a moving lens arranged in an image pickup apparatus of an endoscope is set as a minute amount, for example, a range of 0.3 to 1.0 mm.

Meanwhile, for moving mechanisms that move a moving lens frame in an image pickup apparatus, e.g., mechanisms that advance and retract a wire connected to a moving lens frame via an operation lever or a drive motor provided in an operation section, or mechanisms including an urging spring and a shape memory alloy provided in an insertion portion of an endoscope to advance and retract a moving lens frame by means of energization and stopping energization are known.

For example, Japanese Patent Application Laid-Open Publication No. 2007-229155 discloses an endoscope that enables reduction in size of an image pickup unit including an actuator to achieve reduction in diameter of a distal end portion of an insertion portion of the endoscope. The endoscope includes an actuator unit that advances and retracts a moving lens frame in a shooting optical axis direction. The actuator unit includes, e.g., an urging spring and a shape memory alloy (hereinafter referred to as "SMA") wire.

With such actuator unit, the moving lens frame in the image pickup apparatus is moved forward by an urging force of the urging spring in a non-energized state in which the SMA wire is extended, and is moved to the proximal end side by making the SMA wire enter an energized state to make the SMA wire contract against the urging force of the urging spring.

SUMMARY OF THE INVENTION

An image pickup apparatus for an endoscope according to an aspect of the present invention includes: an image pickup device unit including an image pickup device, the image pickup device unit being arranged in a distal end portion of an insertion portion of the endoscope, the insertion portion including the distal end portion, a bending portion and a flexible tube portion continuously provided in this order from a distal end side; a lens unit including a moving lens that moves to a first observation position and a second observation position, the lens unit being included in an objective optical system that forms an optical image on an image pickup surface of the image pickup device; an actuator apparatus for an endoscope, the actuator apparatus including a first elastic member having an urging force that makes a moving lens frame in which the moving lens in the lens unit is disposed be arranged at the first observation, a second elastic member having an urging force larger than the urging force of the first elastic member and making the moving lens frame be arranged at the second observation position, and a shape memory alloy wire having a property of extending/contracting as a result of a temperature thereof changing due to a current applied from an external power supply via an electric cable, the shape memory alloy wire holding the second elastic member in a tensionless state when the shape memory alloy wire is extended, and contracting the second elastic member into a predetermined state and holding the second elastic member when the shape memory alloy wire is contracted; a driving force transmitting wire arranged on a distal end side of the shape memory alloy wire in the actuator apparatus for an endoscope, and having a length longer than a length along an insertion direction of the distal end portion and the bending portion; a pressing member fixed to a distal end portion of the driving force transmitting wire, the pressing member, upon receipt of an elastic force from the second elastic member, pressing the moving lens frame toward the second observation position; and a fixing portion that fixes a proximal end portion of the driving force transmitting wire and a distal end portion of the shape memory alloy wire in an integrated manner in the flexible tube portion.

DETAILED DESCRIPTION OF THE PREFERRED EMBODIMENT

An embodiment of the present invention will be described with reference to FIGS. 1 to 9.

Figure 1:
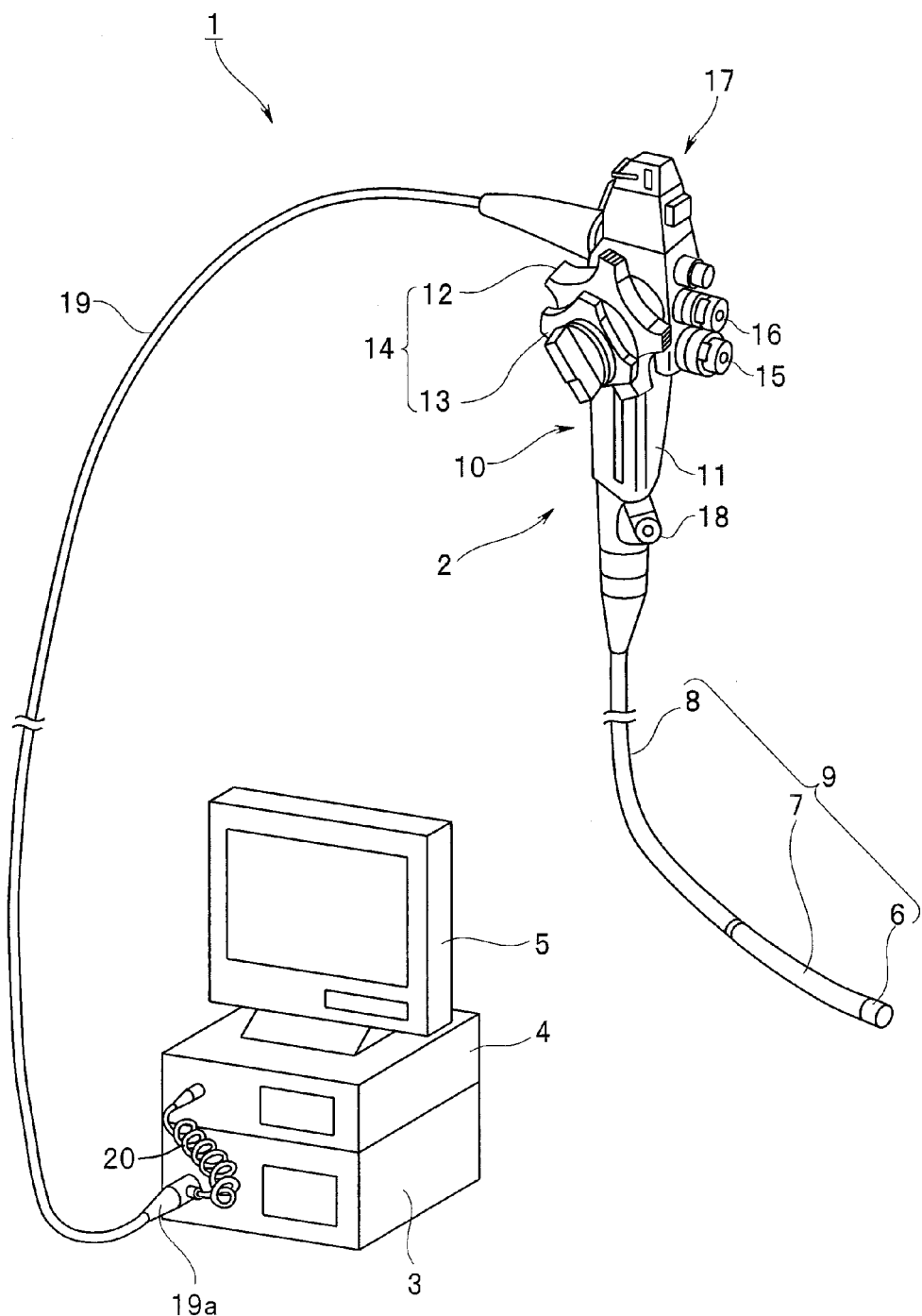
FIG. 1 is a diagram illustrating an endoscope apparatus including an electronic endoscope including an image pickup apparatus that includes an actuator apparatus for an endoscope.

As illustrated in FIG. 1, an electronic endoscope system 1 mainly includes an electronic endoscope (hereinafter abbreviated as "endoscope") 2, a light source apparatus 3, a video processor 4 and a color monitor 5, which is a display apparatus.

The endoscope 2 includes an insertion portion 9, an operation section 10 and a universal cord 19.

The insertion portion 9 includes a distal end portion 6, a bending portion 7 and a flexible tube portion 8 continuously provided in this order from the distal end side, which is one end side. At a distal end face of the distal end portion 6, e.g., a distal end opening, an observation window, a plurality of illumination windows and a cleaning nozzle are disposed. At a rear side of the observation window, an image pickup apparatus including a moving lens frame that can be moved in an optical axis direction within the later-described lens unit is provided. Meanwhile, for example, light guide fibers that convey illuminating light from the light source apparatus 3 face rear sides of the plurality of illumination windows.

The operation section 10 includes an operation section body 11 that doubles as a grasping portion. The operation section body 11 includes a bending operation section 14 that includes bending operation knobs 12 and 13, an air/water sending control section 15, a suction control section 16, and a switch section 17 that includes a plurality of switches. The switch section 17 includes, e.g., switches for operating imaging pickup functions, for example, a zooming function. Reference numeral 18 denotes a forceps opening into which a treatment instrument such as bioptic forceps is inserted.

The universal cord 19 extends from a proximal end side of the operation section 10, and at an end portion thereof, a scope connector 19a is provided. The scope connector 19a is detachably connected to the light source apparatus 3. An end of a cable 20 for an image pickup apparatus is detachably connected to a side portion of the scope connector 19a. Another end of the cable 20 for an image pickup apparatus is detachably connected to the video processor 4.

The light source apparatus 3 according to the present embodiment includes a power supply section as an external power supply that applies a current to a shape memory alloy wire (hereinafter abbreviated as "SMA wire"), which is a wire-like shape memory alloy described later. It should be noted that the power supply section may be provided to the video processor 4.

An image pickup apparatus 30 for an endoscope (hereinafter abbreviated as "image pickup apparatus") provided in the distal end portion 6 will be described with reference to FIGS. 2 to 9.

Figure 2:
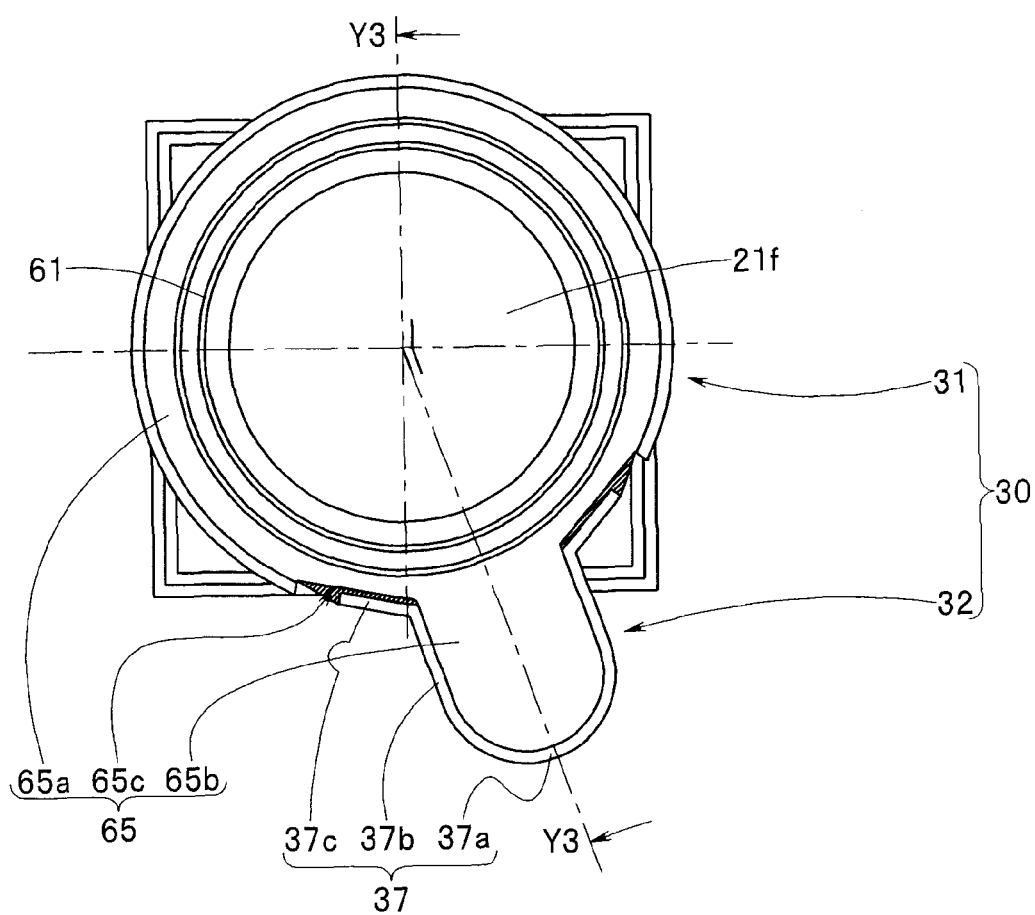
FIG. 2 is a front view of the image pickup apparatus.

As illustrated in FIG. 2, the image pickup apparatus 30 includes an image pickup optical portion 31 that includes a plurality of lenses disposed therein, and a moving mechanism portion 32.

Figure 3:
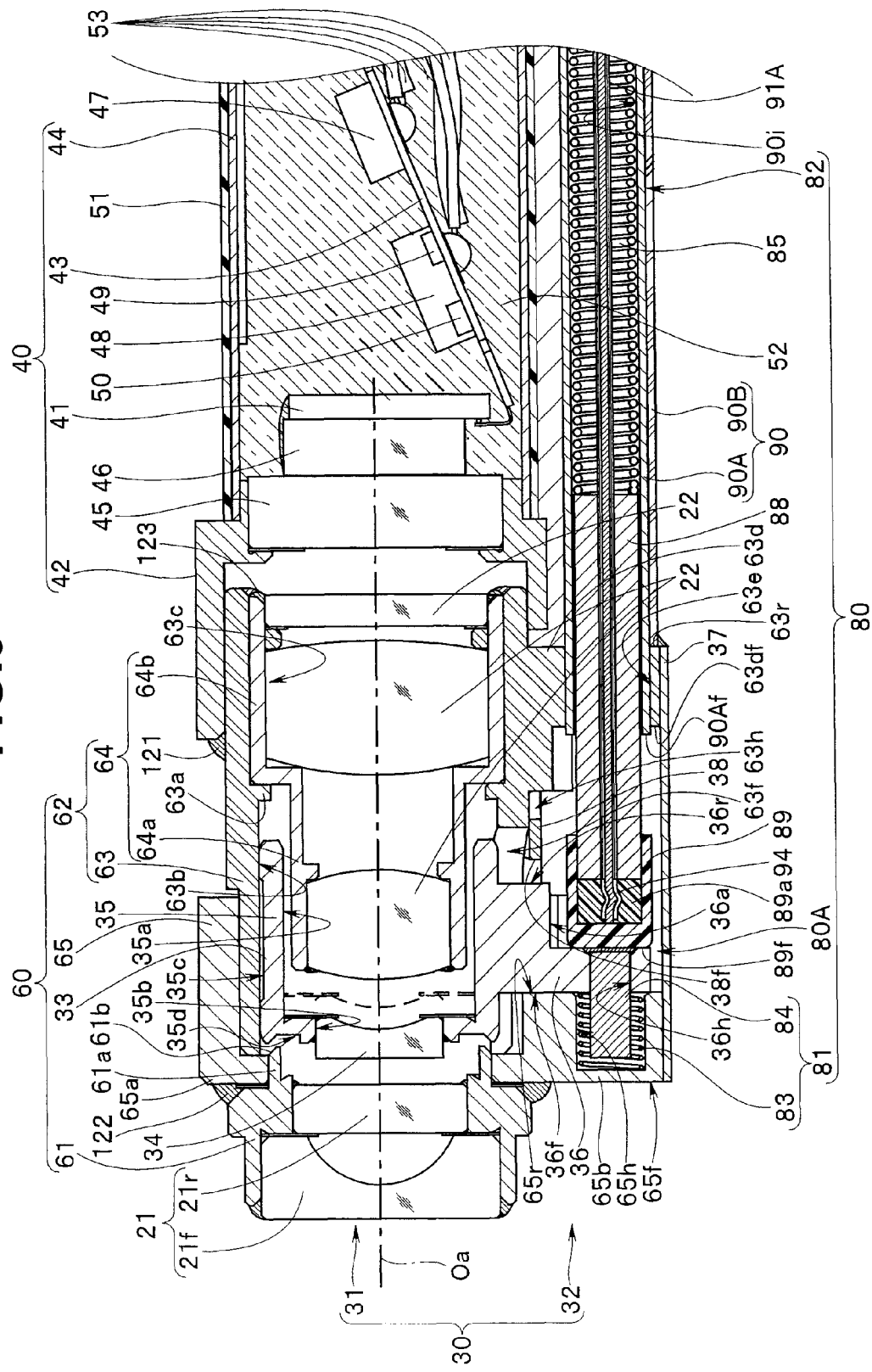
FIG. 3 is a cross-sectional diagram along line Y3-Y3 of FIG. 2.

As illustrated in FIG. 3, the image pickup optical portion 31 mainly includes an image pickup device unit 40 and a lens unit 60. The lens unit 60 includes a moving lens frame 33 that can advance and retract in an optical axis direction. In the moving lens frame 33, at least one optical lens (hereinafter referred to as "moving lens") 34 is disposed.

In the moving mechanism portion 32, an actuator apparatus 80 for an endoscope, which advances and retracts the moving lens frame 33, is disposed. The actuator apparatus 80 for an endoscope includes a first moving mechanism portion 81 and a second moving mechanism portion 82.

The first moving mechanism portion 81 has a function that moves the moving lens frame 33 to the proximal end side and holds the moving lens frame 33 at a first observation position that is a predetermined position on the proximal end side. Meanwhile, the second moving mechanism portion 82 has a function that moves the moving lens frame 33 to the distal end side and holds the moving lens frame 33 at a second observation position that is a predetermined position on the distal end side.

In the present embodiment, the first moving mechanism portion 81 includes a first compression coil spring 83 that is a compression spring. Meanwhile, the second moving mechanism portion 82 includes a second compression coil spring 85 that is a compression spring, and a SMA wire 86, etc., illustrated in FIG. 4. The SMA wire 86 has the characteristic of contracting as the SMA wire 86 is heated by application of a current and extending as the SMA wire 86 is cooled to room temperature by stopping the current application. When the SMA wire 86 is extended, the SMA wire 86 is in a tensionless state.

Figure 5:
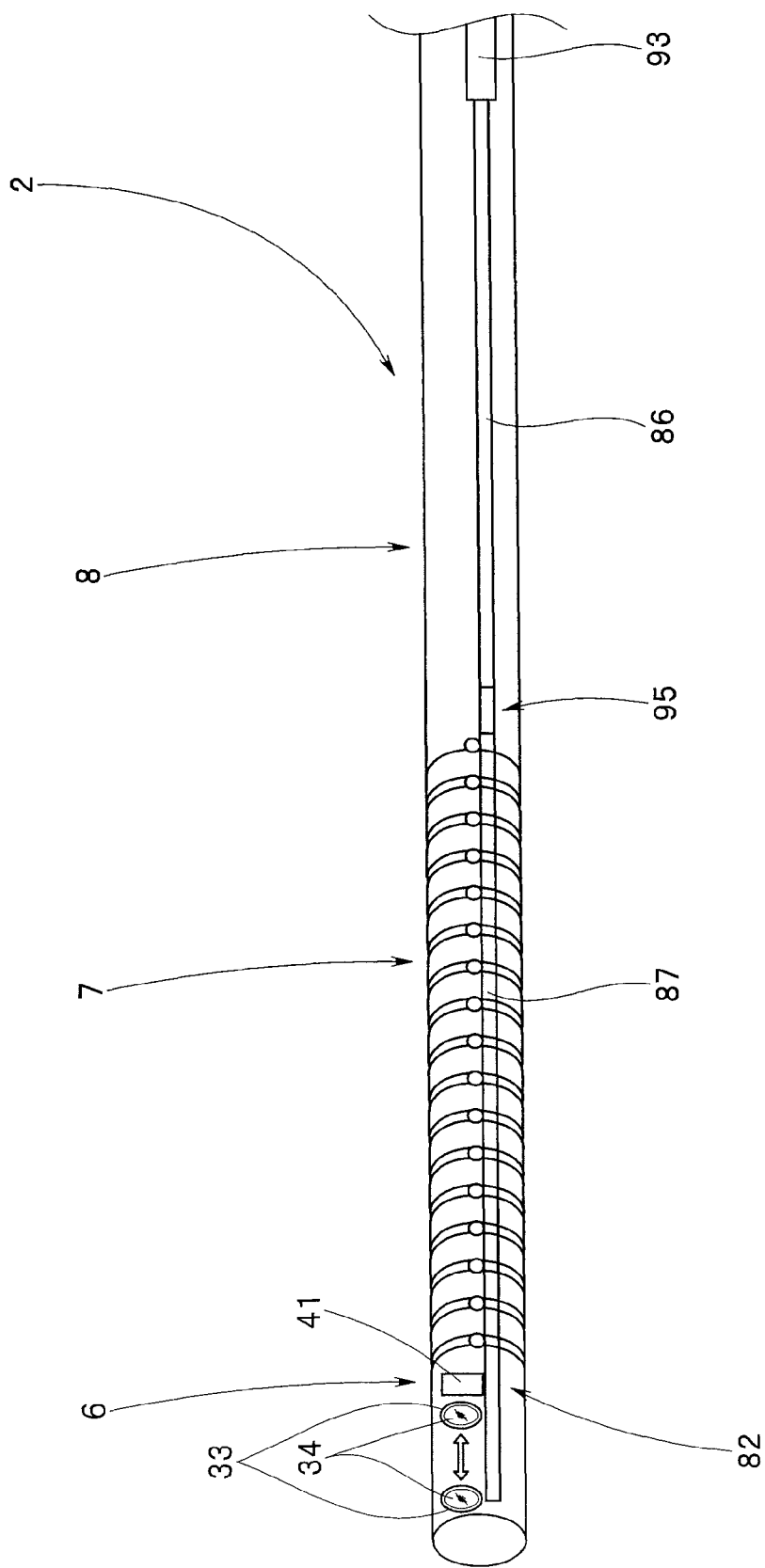
FIG. 5 is a schematic diagram illustrating arrangement of the actuator apparatus for an endoscope in an insertion portion of the endoscope.

In the present embodiment, as illustrated in FIG. 5, the SMA wire 86 is arranged so as to be inserted in the flexible tube portion 8, and a distal end thereof is set to be positioned in the vicinity of the bending portion 7 side of the flexible tube portion 8.

The image pickup device unit 40, the lens unit 60 and the actuator apparatus 80 for an endoscope included in the image pickup apparatus 30 will be described below with reference to the drawings.

First, a configuration of the image pickup device unit 40 will be described with reference to FIG. 3.

The image pickup device unit 40 mainly includes an image pickup device 41, a device frame 42, a circuit substrate 43 and an image pickup device sheathing frame (hereinafter referred to as "sheathing frame") 44.

The image pickup device 41 may be, for example, a CCD (charge coupled device) or a CMOS (complementary metal-oxide semiconductor). The image pickup device 41 is what is called a heat generating element that generates heat in a driven state. For example, two cover lenses 45 and 46, which are optical members, are bonded and fixed on the light-receiving side of the image pickup device 41. The second cover lens 46 is arranged on a light-receiving surface of the image pickup device 41.

The device frame 42 includes, for example, stainless steel. The first cover lens 45 is fixed to an inner face of a proximal end portion of the device frame 42 in an integrated manner by means of, for example, bonding. In other words, the image pickup device 41 is fixed to the device frame 42 via the lenses 46 and 45.

On an inner face of a distal end portion of the device frame 42, a proximal end portion of the later-described first proximal end frame 63 included in the lens unit 60 is arranged. The first proximal end frame 63 and the device frame 42 are integrally joined by means of, for example, solder 121.

Various electronic components 47, 48, 49 and 50, etc., are mounted on the circuit substrate 43. A distal end side of the circuit substrate 43 on which the electronic components 47, 48, 49 and 50 are mounted is electrically connected to the image pickup device 41. A plurality of terminal portions (not illustrated) included in the circuit substrate 43 are connected to distal end portions of the respective corresponding signal wires 53. The signal wires 53 extending from the circuit substrate 43 are bundled as a signal cable. The signal cable extends into the scope connector 19a through the insertion portion 9, the operation section 10 and the universal cord 19.

The sheathing frame 44 covers, e.g., the image pickup device 41, the circuit substrate 43 with the electronic components 47, 48, 49 and 50 mounted thereon and a distal end-side portion of the signal cable. The sheathing frame 44 is formed so as to have a predetermined shape by, for example, rolling or flexing one rectangular thin plate including stainless steel.

Reference numeral 51 denotes a heat shrinkable tube. The heat shrinkable tube 51 covers an outer side of the sheathing frame 44 and provides an outermost sheath of the image pickup device unit 40. Reference numeral 52 denotes an insulating sealing resin.

Figure 6:
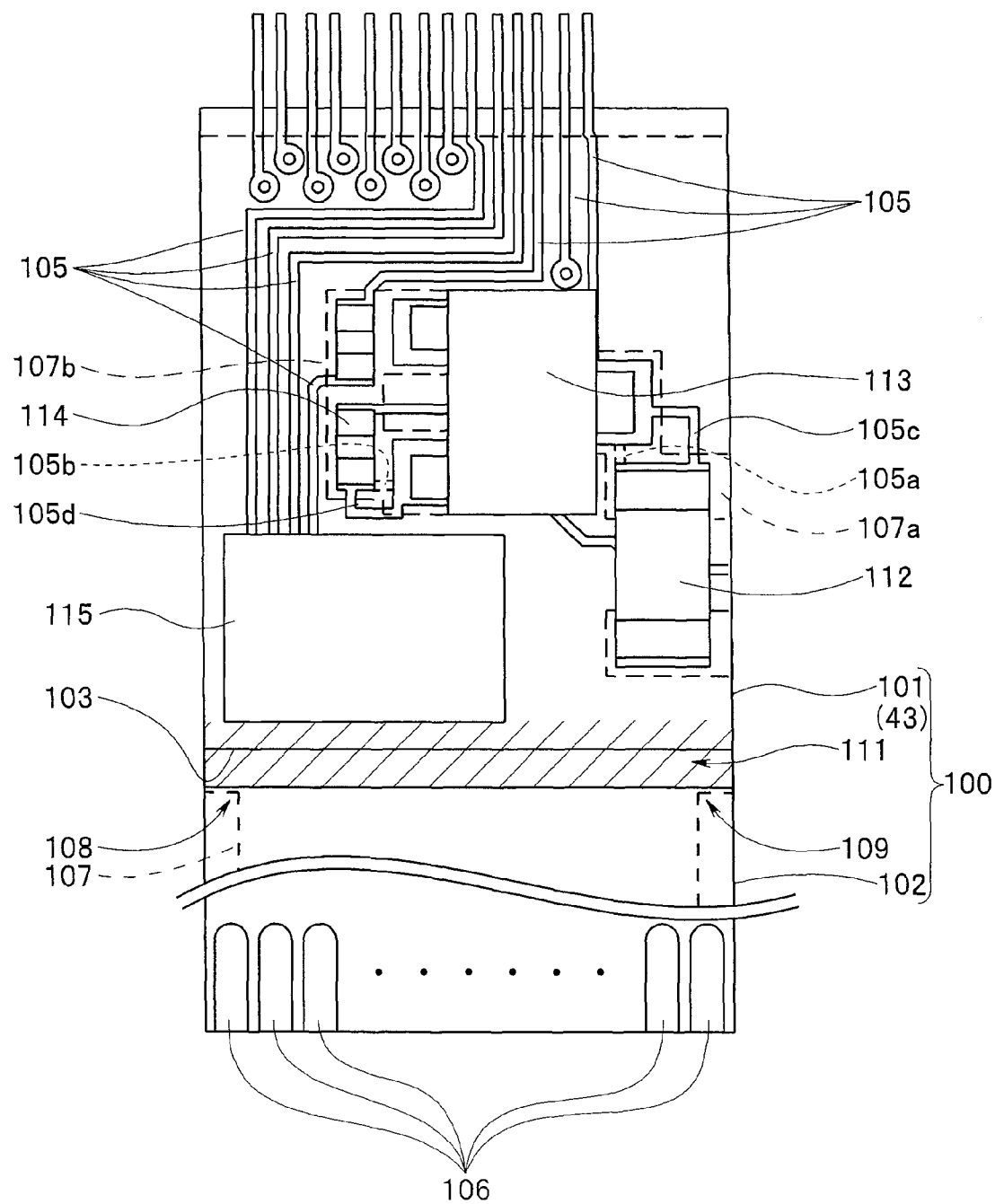
FIG. 6 is an enlarged view of a part of a flexible printed substrate that provides a circuit substrate included in an image pickup device unit in the image pickup apparatus, and is a diagram illustrating a relationship between wirings configured in the circuit substrate and a resist.

The circuit substrate 43 includes, for example, a flexible printed substrate 100 having flexibility, which is illustrated in FIG. 6.

The flexible printed substrate 100 includes a substrate configuring portion 101, which is the circuit substrate 43, and an inspection substrate portion 102. The inspection substrate portion 102 of the flexible printed substrate 100 is cut off, for example, along a cutting line 103 after end of an inspection. The substrate configuring portion 101 of the flexible printed substrate 100 becomes the circuit substrate 43 after the inspection substrate portion 102 is cut off from the flexible printed substrate 100.

The substrate configuring portion 101 includes wirings 105. The inspection substrate portion 102 includes a plurality of inspection terminals 106 on one side. On a surface of the flexible printed substrate 100, a resist 107, which is a protective film, is provided in the shape indicated by the dashed lines.

The flexible printed substrate 100 in the present embodiment is provided with step-like portions 108 and 109 at, for example, predetermined positions of the resist 107 in order to perform the cutoff work easily after the flexible printed substrate 100 passed an acceptance inspection.

Such configuration enables a worker to easily recognize a cutting area 111, which is shaded, by viewing the step-like portions 108 and 109.

In other words, when the worker performs the cutoff work using a non-illustrated cutting tool, the worker sets the flexible printed substrate 100 on the cutting tool. At that time, the worker sets a cutting start position so as to be a position on the substrate configuring portion 101 side relative to the first step-like portion 108 and the second step-like portion 109 and on the inspection substrate portion 102 side relative to the fourth electronic component 115. Subsequently, the worker performs the cutoff work by operating a blade portion of the cutting tool. Then, the inspection substrate portion 102 is cutoff at the cutting area 111, enabling the inspection substrate portion 102 to be efficiently cut off from the flexible printed substrate 100.

Furthermore, in the present embodiment in FIG. 6, for preventing cracking of solder on the wirings connecting the electronic components and preventing displacement of positions where the mounted electronic components are arranged, the resist 107 is provided on the wirings 105 as indicated by the dashed lines.

More specifically, for example, a resist 107a is provided on a wiring 105c connecting the first electronic component 112 and the second electronic component 113. Also, a resist 107b is provided on a wiring 105d connecting the third electronic component 114 and the second electronic component 113.

Such configuration prevents cracking of solder occurring as a result of solder flowing to the wirings 105a and 105b side owing to the wirings 105a and 105b being exposed as indicated by solid lines in FIG. 6, as well as displacement of the electronic components.

Next, a configuration of the lens unit 60 will be described with reference to FIGS. 2 and 3.

The lens unit 60 is an objective optical system that forms an optical image on an image pickup surface of the image pickup device 41 included in the image pickup device unit 40. The lens unit 60 mainly includes the moving lens frame 33, a distal end-side lens frame 61, a proximal end-side lens frame 62, and a lens frame retainer 65. Reference numeral Oa denotes an optical axis of the lens unit 60.

The moving lens frame 33 includes a slide barrel portion 35, and a moving frame projection portion 36 projecting from an outer circumferential face of the slide barrel portion 35. The slide barrel portion 35 is included in the image pickup optical portion 31, and the moving frame projection portion 36 is included in the moving mechanism portion 32. The moving lens frame 33 is advanced and retracted by the actuator apparatus 80 for an endoscope.

The slide barrel portion 35 is slidably arranged inside the later-described first proximal end frame 63 of the proximal end-side lens frame 62. In the slide barrel portion 35, for providing a longest possible fit length, opposite ends of the barrel portion 35 are subjected to round chamfering (hereinafter referred to as R-chamfering) and then opposite side faces are cut to make the length of the barrel portion 35 be a predetermined length.

Figure 7A:
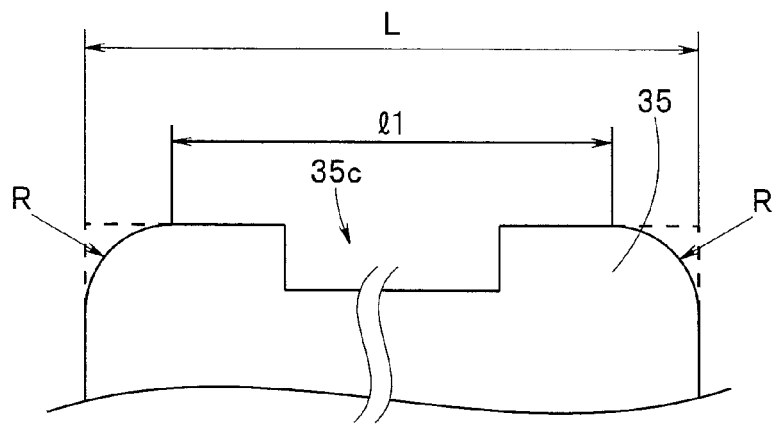
FIG. 7A is a diagram illustrating common chamfers.

In general, R-chamfering is performed to opposite ends of the slide barrel portion 35 after processing is performed to make the length of the slide barrel portion 35 be a predetermined length L as illustrated in FIG. 7A. Consequently, a fit portion I is formed in a longitudinal direction of the slide barrel portion 35.

Figure 7B:
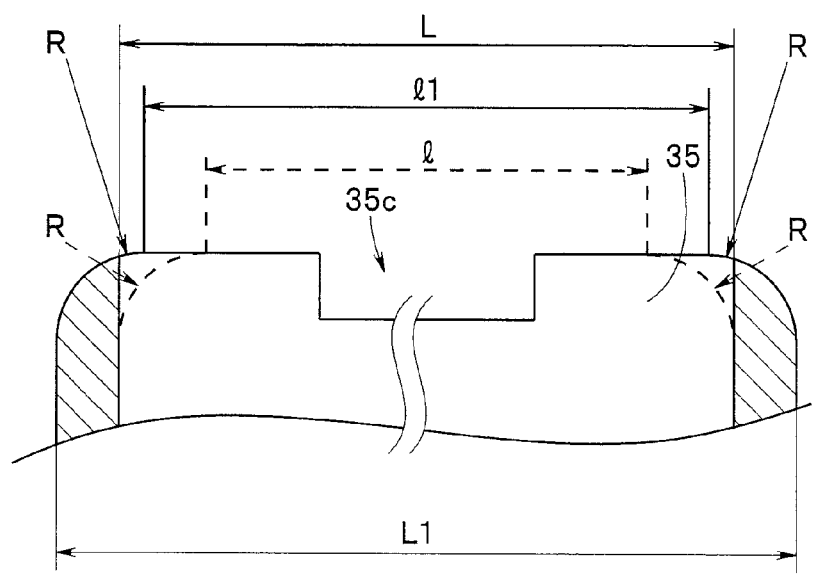
FIG. 7B is a diagram illustrating chamfers for providing a large fit length.

Meanwhile, in the present embodiment, as illustrated in FIG. 7B, processing is performed in advance to make the length of slide barrel portion 35 be, for example, a length L1 that is longer than the length L.

Next, R-chamfering indicated by solid lines is performed on opposite ends of the slide barrel portion 35. Next, the opposite side faces are cut to each have a predetermined length as indicated by hatching in the Figure so that a part of the R-chamfering remains, thereby processing the slide barrel portion 35 so as to have the length L. Consequently, a fit portion I1 is formed in the longitudinal direction of the slide barrel portion 35. The fit portion I1 formed as described above can have a long fit length compared to the fit portion I formed as a result of R-chamfering as indicated by the dashed lines.

Reference numeral 35c denotes a resistance reduction groove. The resistance reduction groove 35c having a predetermined width is provided in a circumferential direction on an outer circumferential face of the slide barrel portion 35, whereby a resistance to sliding between slide barrel portion 35 and the first proximal end frame 63 is reduced while a long fit length of the slide barrel portion 35 is provided, enabling favorable slidability.

The slide barrel portion 35 includes a barrel space 35a. A small diameter portion 64a, which will be described later, of the proximal end-side lens frame 62 is arranged so as to loosely fit in the barrel space 35a. The slide barrel portion 35 includes a lens hole 35b that makes the barrel space 35a and the outside be in communication with each other. The moving lens 34 is fixedly provided in the lens hole 35b. A recess portion 36a and a core bar hole 36h are formed in the moving frame projection portion 36. In the recess portion 36a, a distal end side of the later-described contact member 89 included in the second moving mechanism portion 82 is arranged. A core bar 84, which is a guide pin, is arranged in the core bar hole 36h. The through hole 36h is a communication hole that makes the recess portion 36a and the outside be in communication with each other. A center axis of the core bar hole 36h is parallel to the optical axis Oa.

The core bar 84, which is arranged in an inner hole of the first compression coil spring 83, prevents buckling of the spring 83 that extends and contracts. The core bar 84 is fixed to the core bar hole 36h in an integrated manner by means of, for example, bonding. A proximal end face of the first compression coil spring 83 is arranged so as to be in contact with a distal end face 36f of the moving frame projection portion 36.

A first optical lens group 21 including a plurality of optical members, and a diaphragm, etc., are fixedly provided in the distal end-side lens frame 61. As the first optical lens group 21, for example, a distal end lens 21f and a proximal end lens 21r are fixedly provided in the distal end-side lens frame 61. In the present embodiment, the proximal end lens 21r is brought into contact with a back face of the distal end lens 21f to provide a space between the proximal end lens 21r and the moving lens 34. Consequently, an endoscope image of a desired observation region can be obtained by movement of the moving lens 34 within the space.

At a proximal end side of the distal end-side lens frame 61, a ring-shaped lens frame retainer projection portion 61a is formed. The lens frame retainer projection portion 61a includes a space that receives the moving lens 34 and an outer circumferential face that fixes the lens frame retainer 65. On an outer circumferential face of the lens frame retainer projection portion 61a, a lens frame retainer 65 is arranged and joined to the distal end-side lens frame 61 in an integrated manner, by means of, for example, solder 122.

The lens frame retainer projection portion 61a is configured so as to project by a preset amount to provide a strength enabling the lens frame retainer 65 to be reliably joined and fixed to the distal end-side lens frame 61. An edge on an outer circumferential side of a proximal end portion of the lens frame retainer projection portion 61a is cut off so as to form a cut surface 61b. Meanwhile, on a distal end face side of the slide barrel portion 35, a circumferential, projection portion proximal end portion relief groove 35d is provided. The outer circumference of the proximal end portion of the lens frame retainer projection portion 61a, which includes the cut surface 61b, is received in the projection portion proximal end portion relief groove 35d.

As described above, the lens frame retainer projection portion 61a is made to project on the proximal end side of the distal end-side lens frame 61, and the projection portion 61a is received in the projection portion proximal end portion relief groove 35d. As a result, a decrease in fit length of the moving lens frame 33 can be prevented and a joining strength enabling the lens frame retainer 65 to be reliably fixed to the distal end-side lens frame 61 is provided.

The proximal end-side lens frame 62 includes, two frames, i.e., the first proximal end frame 63 and a second proximal end frame 64. The first proximal end frame 63 and the second proximal end frame 64 are joined and integrated via solder 123 provided on the respective proximal end face sides, providing the proximal end-side lens frame 62.

The first proximal end frame 63 includes a circumferential projection portion 63a at a predetermined position of an inner face. The circumferential projection portion 63a divides an inner space of the first proximal end frame 63 into a moving lens frame sliding space 63b and a second proximal end frame arranging space 63c.

A large diameter portion 64b, which will be described later, of the second proximal end frame 64 is arranged in the second proximal end frame arranging space 63c in the first proximal end frame 63. At a predetermined position in an outer circumferential face on the second proximal end frame arranging space 63c side of the first proximal end frame 63, a proximal end-side lens frame projection portion 63d that projects externally is provided.

The proximal end-side lens frame projection portion 63d is included in a proximal end side of a moving mechanism arranging portion. A guide tube hole 63e is formed in the proximal end-side lens frame projection portion 63d. A first pipe 90A of the later-described guide pipe 90, which is included in the actuator apparatus 80 for an endoscope, is fixedly provided in the guide tube hole 63e. A center axis of the guide tube hole 63e is parallel to the optical axis.

In the moving lens frame sliding space 63b, the slide barrel portion 35 of the moving lens frame 33 is slidably arranged. At a predetermined position on the moving lens frame sliding space 63b side of the first proximal end frame 63, a cutout groove 63f is formed. The cutout groove 63f makes the moving lens frame sliding space 63b and the outside be in communication with each other.

The cutout groove 63f guides the moving frame projection portion 36 that projects from the slide barrel portion 35 arranged in the moving lens frame sliding space 63b to the outside relative to the outer circumferential face of the first proximal end frame 63. Also, the cutout groove 63f provides a movement space in which the moving frame projection portion 36 is arranged so as to freely advance and retract in the optical axis direction.

The cutout groove 63f is formed so as to have a width larger than a width of the moving frame projection portion 36. A length of the cutout groove 63f is set taking a distance of sliding of the moving lens frame 33 into consideration.

The second proximal end frame 64 includes the small diameter portion 64a on the distal end side having a stepped shape, and the large diameter portion 64b on the proximal end side. The second optical lens group 22 including a plurality of optical members, and a diaphragm, etc., are fixedly provided on an inner face of the small diameter portion 64a and an inner face of the large diameter portion 64b. The small diameter portion 64a and the large diameter portion 64b are continuously provided by, for example, an inclined surface (not illustrated) or a step portion, which is illustrated in the Figure.

The small diameter portion 64a of the second proximal end frame 64 is arranged so as to loosely fit in the moving lens frame sliding space 63b of the first proximal end frame 63. As a result of arranging the small diameter portion 64a in the moving lens frame sliding space 63b, only the slide barrel portion 35 of the moving lens frame 33 is arranged in the moving lens frame sliding space 63b of the first proximal end frame 63. As a result, the moving lens frame sliding space 63b and the moving lens frame 33 are properly formed to provide a sufficient fit length, enabling the moving lens frame 33 to be stably moved in the optical axis direction.

In the present embodiment, the outer circumferential face of the slide barrel portion 35 and an inner face of the moving lens frame sliding space 63b, which are sliding surfaces, are not subjected to plating processing for preventing generation of flare or ghost caused by reflection. As described above, omission of plating processing on the sliding surface enhances the slidability of the slide barrel portion 35 in the moving lens frame sliding space 63b.

Such configuration enables eliminating the need for secondary processing to remove the plating from the outer circumferential face of the slide barrel portion 35 and the inner surface of the moving lens frame sliding space 63b. Accordingly, the problem of poor sliding occurring as a result of the secondary processing can be solved.

The lens frame retainer 65 includes a retainer barrel portion 65a, and a retainer projection portion 65b that projects from a predetermined position of an outer circumferential face of the retainer barrel portion 65a. The retainer projection portion 65b is included in the distal end side of the moving mechanism arranging portion.

The retainer barrel portion 65a makes the distal end-side lens frame 61 and the first proximal end frame 63 included in the proximal end-side lens frame 62 be joined and fixed to each other via, e.g., an adhesive or solder. At a predetermined position in the retainer projection portion 65b, a hole 65h, which is a recess portion for the first compression coil spring 83 to be arranged therein, is formed. At a proximal end face 65r side of the retainer projection portion 65b, an opening of the hole 65h is formed. A depth of the hole 65h is set so that the first compression coil spring 83 having a predetermined urging force projects from the opening by a predetermined amount.

The reference numeral 37 denotes a cover member. The cover member 37 includes a semicircular shape portion 37a, a pair of flat portions 37b and a pair of wing-shape portions 37c. The pair of flat portions 37b stands from the semicircular shape portion 37a in such a manner that the flat portions 37b are opposed to each other. The pair of wing-shape portions 37c is formed so as to open up from end portions of the respective flat portions 37b toward the outside. The semicircular shape portion 37a and the flat portions 37b are arranged on and fixed to the retainer projection portion 65b and the projection part of the proximal end-side lens frame projection portion 63d by means of, for example, bonding. The pair of wing-shape portions 37c is fixed to a first recessed portion 65c formed at circumferential faces on opposite sides of the retainer projection portion 65b, which are included in the outer circumferential face of the barrel portion 65a, and a non-illustrated second recessed portion formed on circumferential faces on the opposite sides of the proximal end-side lens frame projection portion 63d, which are included in the outer circumferential face of the first proximal end frame 63, by means of, for example, bonding.

Consequently, an opening of the moving mechanism arranging space portion 80A configured between the retainer projection portion 65b included in the distal end side of the moving mechanism arranging portion and the proximal end-side lens frame projection portion 63d included in the proximal end side of the moving mechanism arranging portion is blocked by the cover member 37 in a water-tight manner.

Consequently, the hole 65h in which the first compression coil spring 83 is arranged is formed in the retainer projection portion 65b, while the core bar hole 36h in which the core bar 84 is arranged is formed in the moving frame projection portion 36. In addition, the opening of the moving mechanism arranging space portion 80A configured between the retainer projection portion 65b and the proximal end-side lens frame projection portion 63d is closed up by the cover member 37. Consequently, the water tightness of the moving mechanism arranging space portion 80A can substantially be enhanced.

Lastly, the actuator apparatus 80 for an endoscope will be described with reference to FIGS. 3 to 5, 8 and 9.

As described above, the the actuator apparatus 80 for an endoscope includes the first moving mechanism portion 81 and the second moving mechanism portion 82.

The first moving mechanism portion 81 includes the first compression coil spring 83, which is a compression spring, and the core bar 84. The first compression coil spring 83 has an urging force that makes the moving lens frame 33 be arranged so as to be in contact with a proximal end position adjusting ring 38 and holds such arrangement state. The proximal end position adjusting ring 38 is a member that defines an enlarged observation position.

The first compression coil spring 83 projects from the opening of the hole 65h by a predetermined amount to move the moving frame projection portion 36 to the first observation position and holds the moving frame projection portion 36 at that position, in a state in which no urging force toward an distal end of the optical axis is imposed on the moving frame projection portion 36 from the second moving mechanism portion 82.

The proximal end position adjusting ring 38 has a C-ring shape. The proximal end position adjusting ring 38 is arranged so as to be engaged in a C-ring arranging groove 63h formed on the outer circumferential face of the first proximal end frame 63 so as to have a preset width. A distal end face 38f of the proximal end position adjusting ring 38 provides a moving lens frame proximal end-side restricting surface, and a proximal end-side positioning surface 36r of the moving frame projection portion 36 is in contact with the distal end face 38f. The proximal end position adjusting ring 38 is fixed to the C-ring arranging groove 63h by means of, for example, bonding after position adjustment of, e.g., the focus at the enlarged observation position being performed by moving the moving lens frame 33 within the C-ring arranging groove 63h.

With such configuration, it is possible that the distal end-side lens frame 61 and the proximal end-side lens frame 62 are bonded and fixed via the retainer barrel portion 65a and then the proximal end position adjusting ring 38 is fixed to the C-ring arranging groove 63h of the first proximal end frame 63. As a result, the problem of an adhesive adhering to the proximal end position adjusting ring 38 when the distal end-side lens frame 61 and the proximal end-side lens frame 62 are bonded and fixed to each other can be solved.

Figure 4:
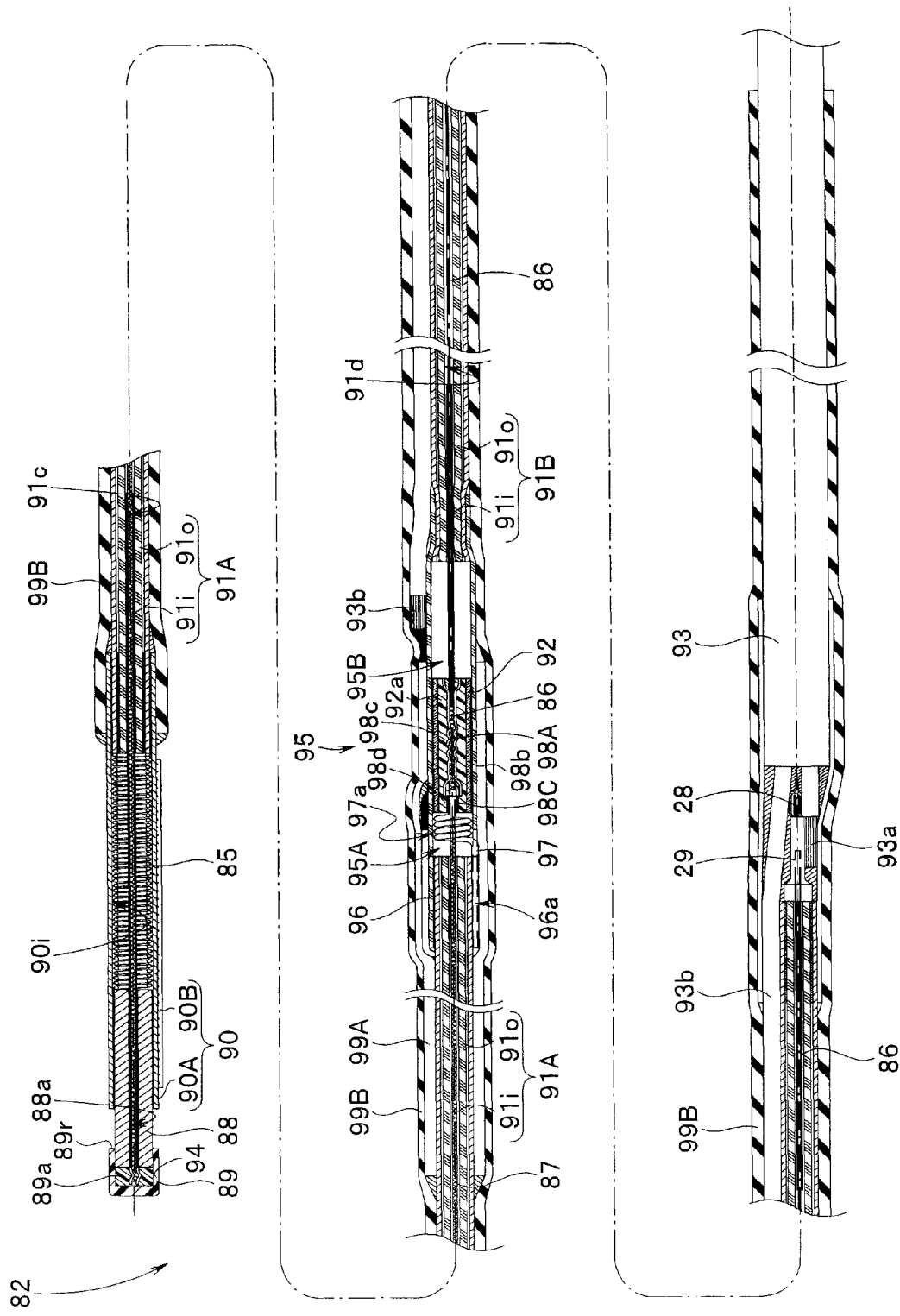
FIG. 4 is a diagram illustrating a configuration of the actuator apparatus for an endoscope.

As illustrated in FIG. 4, the second moving mechanism portion 82 mainly includes the second compression coil spring 85, which is a second elastic member, the SMA wire 86, a driving force transmitting wire 87, a tubular pressing member 88, the contact member 89, the guide pipe 90, insulating tubes 91A and 91B, a connection portion covering pipe 92 and an electric cable 93. The driving force transmitting wire 87 is a stainless steel wire having a preset stiffness and flexibility.

The guide pipe 90 includes a tubular first pipe 90A that provides an inner layer side and a U-shape second pipe 90B that provides an outer layer side. The second pipe 90B is arranged at a predetermined position on the first pipe 90A, and integrated with the first pipe 90A by means of solder or an adhesive.

As illustrated in FIGS. 3 and 4, the distal end side of the first pipe 90A included in the guide pipe 90 is inserted into a guide tube hole 63e formed at the proximal end-side lens frame projection portion 63d of the proximal end-side lens frame 62. After the first pipe 90A is inserted into the guide tube hole 63e, a distal end face of the second pipe 90B is brought into contact with a proximal end face 63r of the proximal end-side lens frame projection portion 63d. Consequently, a distal end face 90Af of the first pipe 90A projects by a predetermined amount relative to a distal end face 63df of the proximal end-side lens frame projection portion 63d. The guide pipe 90 is fixed to the projection portion 63d in an integrated manner by means of, e.g., solder or an adhesive, with the distal end face of the second pipe 90B in contact with the proximal end face 63r of the proximal end-side lens frame projection portion 63d.

Consequently, the guide pipe 90 is configured by the first pipe 90A providing the inner layer side and the second pipe 90B providing the outer layer side, and the second pipe 90B is fixedly provided at the predetermined position on the first pipe 90A. Consequently, the work of attaching the guide pipe 90 to the lens frame projection portion 63d can easily be performed.

A proximal end face 89r of the contact member 89 is in contact with the distal end face of the first pipe 90A. An outer diameter of the contact member 89 is set to be smaller than a diameter of the guide tube hole 63e. With such configuration, the contact member 89 can reliably be prevented from fitting in the guide tube hole 63e. Furthermore, a distal end-side portion of the second moving mechanism portion 82 can freely be inserted into/extracted from the guide tube hole 63e.

A length of the driving force transmitting wire 87 is set to be a predetermined length. More specifically, a distal end portion of the driving force transmitting wire 87 is fixed to the contact member 89 in an integrated manner, and a proximal end portion of the driving force transmitting wire 87 is fixed to a distal end portion of the SMA wire 86 at a position in the vicinity of the bending portion 7 side of the inside of the flexible tube portion 8. Meanwhile, a proximal end portion of the SMA wire 86 fixed to the driving force transmitting wire 87 in an integrated manner is set so as to be located at a predetermined position on the proximal end side relative to a distal end of the flexible tube portion 8 included in the insertion portion 9 of the endoscope 2. An electric wire 93a in the electric cable 93, which supplies a current to the SMA wire 86, is connected to the proximal end portion of the SMA wire 86.

The electric wire 93a is connected to a copper crimp member 29 fixed to the proximal end portion of the SMA wire 86 by means of crimping. At a rear side of the copper crimp member 29, a retaining crimp 28 is provided. At least one turn of the SMA wire 86 is provided around the retaining crimp 28 and then the retaining crimp 28 is fixed to the copper crimp member 29 by means of crimping. Consequently, the proximal end portion of the SMA wire 86 is reliably fixed to the copper crimp member 29 without coming off from the copper crimp member 29.

In such configuration, the retaining crimp 28 with the proximal end side portion of the SMA wire 86 wound therearound is fixed to the copper crimp member 29 by means of crimping, and subsequently, the copper crimp member 29 and the retaining crimp 28 are fixed to each other by solder, and subsequently, the electric cable 93 is soldered to the copper crimp member 29, and subsequently, the copper crimp member 29, the retaining crimp 28 and the electric cable 93 are fixed to one another via an adhesive. Consequently, the durability of connection between the SMA wire 86 and the electric wire 93a is substantially enhanced.

The driving force transmitting wire 87 is inserted in a through hole 88a of the pressing member 88, an inner hole of the second compression coil spring 85, a through hole 91c of the first insulating tube 91A and the connection portion covering pipe 92. Meanwhile, the SMA wire 86 is inserted in the connection portion covering pipe 92 and the through hole 91d of the second insulating tube 91B.

The pressing member 88, the second compression coil spring 85 and the first insulating tube 91A are disposed in an inner hole 90i of the first pipe 90A included in the guide pipe 90. More specifically, on the distal end side of the inner hole 90i, a portion from a center part to a proximal end of the pressing member 88 is disposed, and on the proximal end side of the inner hole 90i, a distal end portion of the first insulating tube 91A is disposed, and at an inner hole center between the proximal end of the pressing member 88 disposed in the inner hole 90i and the distal end of the first insulating tube 91A, the second compression coil spring 85 is disposed.

The second compression coil spring 85 and the pressing member 88 are arranged so as to be slidable relative to the inner hole 90i. Meanwhile, the distal end portion of the first insulating tube 91A is fixed in the inner hole 90i in an integrated manner by means of, for example, bonding. Consequently, a position of a proximal end face of the second compression coil spring 85 is restricted and the second compression coil spring 85 has a variable assembled length.

The second compression coil spring 85 is selected and assembled so that a spring force can be adjusted by a diameter of the SMA wire 86, or is assembled with a position thereof relative to the first pipe 90A of the first insulating tube 91A adjusted.

An urging force of the second compression coil spring 85 disposed in the inner hole 90i of the guide pipe 90 is set to be larger than an urging force of the first compression coil spring 83. Accordingly, the second compression coil spring 85 can move the moving lens frame 33 arranged at the first observation position by means of the urging force of the first compression coil spring 83, by means of the urging force the spring 85 has. More specifically, the second compression coil spring 85 can bring the distal end face 36f of the moving frame projection portion 36 into contact with the proximal end face 65r of the lens frame retainer 65 against the urging force of the first compression coil spring 83 and hold such state.

As a result of the distal end face 36f of the moving frame projection portion 36 of the moving lens frame 33 being brought into contact with the proximal end face 65r of the lens frame retainer 65, the moving lens frame 33 is arranged at a wide-angle observation position, which is the second observation position.

A contact member 89 formed into a cylindrical shape using an insulating member is fixedly provided at a distal end portion of the pressing member 88. The distal end portion of the driving force transmitting wire 87 is disposed in an inner space of the contact member 89, and fixedly provided at the contact member 89 by provision of a bonding portion 89a.

A retaining member 94 is fixedly provided at the distal end portion of the driving force transmitting wire 87 fixedly provided in the inner space of the contact member 89, in order to prevent the driving force transmitting wire 87 from coming off from the contact member 89. The retaining member 94 is a crimp tube, and the distal end portion of the driving force transmitting wire 87 drawn from the through hole 88a of the pressing member 88 is inserted and arranged in the retaining member 94. The retaining member 94 is attached to the distal end portion of the wire 87 in an integrated manner by means of provision of a crimp.

Such configuration enables enhancement in assemblability and size reduction with a simple configuration, and the distal end portion of the driving force transmitting wire 87 to be prevented from coming off from the contact member 89 and reliably fixed to the contact member 89.

The first insulating tube 91A includes a first tube 91i arranged on the inner layer side and a second tube 91o arranged on the outer layer side. The second insulating tube 91B also includes a first tube 91i and a second tube 91o. The first tube 91i is, for example, a PTFE tube including fluorine, and is provided to provide favorable sliding of the driving force transmitting wire 87. Meanwhile, the second tube 91o is, for example, a PEEK tube, and is provided to enhance the stiffness such as efficient transmission of a driving force from the SMA wire 86.

The insulating tubes 91A and 91B each have a double structure including the first tube 91i, which is a PTFE tube, and the second tube 91o, which is a PEEK tube. As a result, friction with the driving force transmitting wire 87 and the SMA wire 86 is reduced by the first tube 91i. Meanwhile, the driving transmission, or the durability for a load during the insertion portion being bent or during assembling can be enhanced by the second tube 91o. Furthermore, the first tube 91i and the second tube 91o are fixed to each other only on one side by means of an adhesive.

Here, connection between the driving force transmitting wire 87 and the SMA wire 86 will be described.

The proximal end portion of the driving force transmitting wire 87 and the distal end portion of the SMA wire 86 are connected at a wire connecting portion 95.

At the wire connecting portion 95, an insulating tube connection pipe (hereinafter abbreviated as "connection pipe") 96 including a metal pipe that includes, for example, stainless steel is provided. On the distal end side of the connection pipe 96, a cutout 96a that makes an inner hole of the pipe and the outside be in communication with each other. The cutout 96a is formed so as to have a width taking a diameter of a ground-side solid wire (hereinafter abbreviated as "solid wire") 97 into consideration. The cutout 96a is formed so as to have a length taking, e.g., the position of the distal end side of the first insulating tube 91A and the number of turns of the solid wire 97 into consideration.

The first insulating tube 91A, the connection portion covering pipe 92 and the second insulating tube 91B are disposed in a pipe inner hole 96i of the connection pipe 96.

More specifically, on the distal end side of the pipe inner hole 96i, the proximal end portion of the first insulating tube 91A is disposed. On the proximal end side of the pipe inner hole 96i, a distal end portion of the second insulating tube 91B is disposed. Furthermore, the connection portion covering pipe 92 is disposed at an inner hole center between the proximal end of the first insulating tube 91A and the distal end of the second insulating tube 91B, which are disposed in the pipe inner hole 96i. A solid wire space 95A is formed between the proximal end of the first insulating tube 91A and the distal end of the connection portion covering pipe 92. Meanwhile, a sliding space 95B is formed between a proximal end of the connection portion covering pipe 92 and the distal end of the second insulating tube 91B.

The connection portion covering pipe 92 is arranged so as to be slidable relative to the pipe inner hole 96i. Therefore, the connection portion covering pipe 92 includes a resin material exhibiting good slidability. Also, the distal end portion of the second insulating tube 91B is bonded and fixed to the connection pipe 96 after a proximal end portion of the connection pipe 96 is crimped. Consequently, a predetermined fixing strength can be obtained while the bond and fit length is decreased.

The proximal end of the first insulating tube 91A is bonded and fixed to the connection pipe 96.

The driving force transmitting wire 87 and the SMA wire 86 are arranged so as to be inserted in the first crimp pipe 98A having stiffness and electrical conductivity, the first crimp pipe 98A including, for example, stainless steel. The first crimp pipe 98A includes first crimps 98b.

Figure 8:
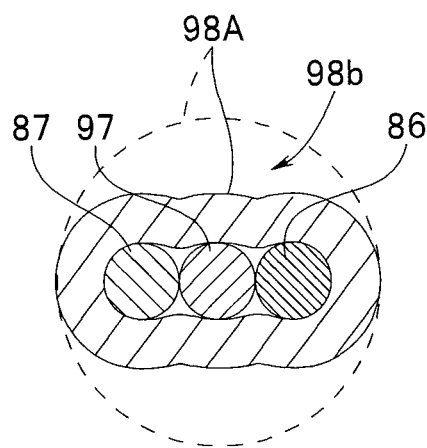
FIG. 8 is a diagram illustrating a driving force transmitting wire and an SMA wire arranged in parallel integrally fixed in a first crimp pipe by first crimps being provided to the first crimp pipe.

The first crimps 98b are wave-like crimps plurally formed at a predetermined interval in an axis direction in order to obtain a desired fixing strength. As illustrated in FIG. 8, the driving force transmitting wire 87, the solid wire 97 and the SMA wire 86 arranged in parallel in the first crimp pipe 98A indicated by the dashed line are fixed in an integrated manner by providing the first crimps 98b to squash the pipe 98A so as to deform. In such fixed state, the solid wire 97 and the SMA wire 86 are electrically connected and firmly fixed in an integrated manner.

Figure 9:
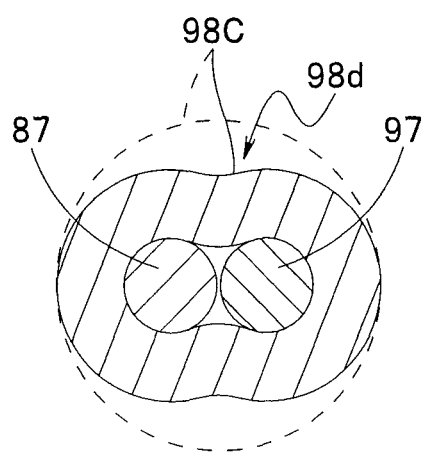
FIG. 9 is a diagram illustrating a solid wire and a driving force transmitting wire integrally fixed in a second crimp pipe by a second crimp being provided to the second crimp pipe.

Furthermore, the driving force transmitting wire 87 is arranged so as to be inserted in the connection portion covering pipe 92 having excellent slidability and including, for example, PEEK. The second crimp pipe 98C is intended to reduce a load imposed on a solder connection portion between the driving force transmitting wire 87 and the later-described solid wire 97. As illustrated in FIG. 9, the solid wire 97 and the driving force transmitting wire 87 in the second crimp pipe 98C are aligned vertical to a crimping direction of a second crimp 98d, and a desired fixing strength can be obtained by application of an adhesive to bond and fix the solid wire 97 and the driving force transmitting wire 87 in addition to the crimp fixing.

The first crimp pipe 98A and the second crimp pipe 98C are arranged at a predetermined position in the connection portion covering pipe 92, and received in the connection portion covering pipe 92 with an insulating adhesive 92a charged therein.

The solid wire 97 extending from a distal end side of the first crimp pipe 98A includes a winding portion 97a in the vicinity of a distal end side of the connection portion covering pipe 92. The winding portion 97a is formed by, for example, thermally deforming the solid wire 97 to be wounded into a plurality of turns in a spiral shape. The winding portion 97a is arranged in the solid wire space 95A.

The solid wire 97 extends from the solid wire space 95A to the distal end of the connection pipe 96 via the cutout 96a and at its distal end side, is folded back toward a proximal end thereof. An end portion of the folded solid wire 97 is fixed by solder to an outer circumferential face of the connection pipe 96 in an integrated and electrically conductive manner at a position away from the distal end of the connection pipe 96 by a predetermined distance.

A portion from the proximal end side of the first insulating tube 91A where the distal end side of the connection pipe 96 is exposed to the proximal end portion of the solid wire 97 connected to the connection pipe 96 is covered by a heat shrinkable tube 99A. As a result of the cutout 96a being covered by the heat shrinkable tube 99A, the cutout 96a is closed up and protected against entrance of moisture.

A ground wire 93b inserted in the electric cable 93 is connected to an outer circumferential face of the proximal end side of the connection pipe 96 by solder. Consequently, the ground wire 93b inserted in the electric cable 93 and the distal end of the SMA wire 86 are electrically connected via the connection pipe 96 and the solid wire 97.

Accordingly, when a current is applied from the power supply section provided in the light source apparatus 3 to the SMA wire 86 via the electric cable 93, a temperature of the SMA wire 86 increases and the SMA wire 86 contracts with the temperature increase.

Then, when the SMA wire 86 reaches a predetermined temperature, the SMA wire 86 contracts and thereby moves the connection portion covering pipe 92 arranged in the connection pipe 96 to the proximal end side of the sliding space 95B. The first crimp pipe 98A with the driving force transmitting wire 87 and the SMA wire 86 fixed therein is received in the connection portion covering pipe 92. Thus, as the connection portion covering pipe 92 is moved, the driving force transmitting wire 87 is pulled and the winding portion 97a of the solid wire 97 turns into an extended state.

Then, as a result of the driving force transmitting wire 87 being pulled with the contraction of the SMA wire 86, the contact member 89 is moved to the proximal end side against the urging force of the second compression coil spring 85 and brought into contact with the distal end face of the first pipe 90A. At this time, the urging force toward the distal end of the optical axis from the second compression coil spring 85 to the moving frame projection portion 36 is cancelled, and the moving lens frame 33 is thereby moved to the first observation position by the urging force of the first compression coil spring 83.

Then, when the current application is stopped again, the temperature of the SMA wire 86 decreases, and with the temperature decrease, the SMA wire 86 is extended. Then, the moving lens frame 33 is moved to the second observation position by the urging force of the second compression coil spring 85.

As described above, the SMA wire 86 is disposed in the flexible tube portion 8 that is away from the distal end portion 6 in which the image pickup device 41, which is a heat generating element, is arranged, via the bending portion 7. Thus, it is possible to reliably prevent the SMA wire 86 in a tensionless state when the SMA wire 86 is cooled to room temperature as a result of the current application being stopped, from contracting as a result of the SMA wire 86 being heated by heat generated by the image pickup device 41. Consequently, the problem of optical characteristics of the image pickup apparatus 30 changing as a result of the moving lens frame 33 being moved during an observation can be improved.

Reference numeral 99B denotes a second heat shrinkable tube, which provides an outermost layer of the second moving mechanism portion 82. Provision of the second heat shrinkable tube 99B for the outermost layer of the second moving mechanism portion 82 enables enhancement in water tightness of the second moving mechanism portion 82.

Furthermore, as the present invention, an image pickup apparatus for an endoscope for what is called a flexible endoscope including a flexible tube portion in an insertion portion has been described. However, the image pickup apparatus for an endoscope may be applied to what is called a rigid endoscope including a rigid insertion portion.

The present invention is not limited only to the above-described embodiment and various alterations are possible without departing from the spirit of the invention.

What is claimed is:

1. An endoscope comprising:
an insertion portion including a distal end portion, a bending portion and a flexible tube portion continuously provided in this order from a distal end side; and
an image pickup apparatus including an image pickup optical portion and a moving mechanism portion arranged in the distal end portion,
wherein the image pickup optical portion includes:
an image pickup device unit including an image pickup device, and
a lens unit including a moving lens that moves to a first observation position and a second observation position, the lens unit being included in an objective optical system that forms an optical image on an image pickup surface of the image pickup device, and
wherein the moving mechanism portion is an actuator apparatus and includes,
a first moving mechanism portion including a first elastic member having an urging force that comes into contact with a distal end surface of a moving frame projection portion of a moving lens frame in which the moving lens in the lens unit is disposed to make the moving lens frame be arranged at the first observation position, and
a second moving mechanism portion including a second elastic member having an urging force larger than the urging force of the first elastic member, the urging force making the moving lens frame be arranged at the second observation position, and a shape memory alloy wire having a property of extending/contracting as a result of a temperature thereof changing due to a current applied from an external power supply via an electric cable, the shape memory alloy wire holding the second elastic member in a tensionless state when the shape memory alloy wire is extended, and contracting the second elastic member into a predetermined state and holding the second elastic member when the shape memory alloy wire is contracted, the shape memory alloy wire having a distal end portion and a proximal end portion arranged in the flexible tube portion of the insertion portion, the distal end portion being positioned on the bending portion side in the flexible tube portion;
wherein the second moving mechanism portion further includes a driving force transmitting wire having a distal end portion fixed to a contact member arranged in a recess portion provided to the moving frame projection portion of the moving lens frame, and a proximal end portion that is fixed to a distal end portion of the shape memory alloy wire in the flexible tube portion of the insertion portion; and wherein the driving force transmitting wire is pulled with contraction of the shape memory alloy wire to cause the contact member fixed to the distal end portion of the driving force transmitting wire to move against the urging force of the second elastic member and cancel the urging force from the second elastic member to the moving frame projection portion.

2. The endoscope according to claim 1, further comprising a pressing member having a distal end portion to which the contact member is fixed, the pressing member having a core hole through which the driving force transmitting wire is passed, the pressing member, upon receipt of an elastic force from the second elastic member, pressing the moving lens frame toward the second observation position.

3. The endoscope according to claim 2, the pressing member includes a cylindrical shape member that is concentric with the driving force transmitting wire.

4. The endoscope according to claim 1, further comprising a fixing portion that fixes a proximal end portion of the driving force transmitting wire and a distal end portion of the shape memory alloy wire in an integrated manner.

5. The endoscope according to claim 4, further comprising:
 a connection portion covering pipe that receives the fixing portion;
 a first insulating tube including a through hole in which the driving force transmitting wire is inserted, and having a distal end portion fixed in an inner hole of a first pipe configuring a guide pipe;
 a second insulating tube including a through hole in which the shape memory alloy wire is inserted; and
 an insulating tube connection pipe including a pipe inner hole, wherein a proximal end portion of the first insulating tube is disposed on a distal end side of the pipe inner hole, a distal end portion of the second insulating tube is disposed on a proximal end side of the pipe inner hole, and the connection portion covering pipe is slidably arranged between the proximal end of the first insulating tube and the distal end of the second insulating tube in the pipe inner hole.

6. The endoscope according to claim 5, wherein the proximal end portion of the driving force transmitting wire and the distal end portion of the shape memory alloy wire are integrally fixed in an electrically conductive manner by providing a crimp to a fixing pipe in a state in which the proximal end portion of the driving force transmitting wire and the distal end portion of the shape memory alloy wire are arranged so as to be inserted in the fixing pipe.

7. The endoscope according to claim 6, wherein the connection pipe is connected with an electric wire in the electric cable, and connected with a solid wire electrically connected to the shape memory alloy wire via the crimp.

8. The endoscope according to claim 5, wherein,
 a solid wire space is formed between a proximal end of the first insulating tube and a distal end of the connection portion covering pipe, the solid wire space being for arranging therein a winding portion formed by winding a ground-side solid wire multiple times in a spiral shape, and
 a sliding space for moving the connection portion covering pipe is formed between a proximal end of the connection portion covering pipe and a distal end of the second insulating tube.

9. The endoscope according to claim 1, further comprising a connection portion covering pipe that receives the fixing portion.

10. The endoscope according to claim 1, further comprising:
 a first insulating tube including a through hole in which the driving force transmitting wire is inserted, and having a distal end portion fixed in an inner hole of a first pipe configuring a guide pipe;
 a second insulating tube including a through hole in which the shape memory alloy wire is inserted;
 an insulating tube connection pipe including a pipe inner hole, wherein a proximal end portion of the first insulating tube is disposed on a distal end side of the pipe inner hole, a distal end portion of the second insulating tube is disposed on a proximal end side of the pipe inner hole, and the connection portion covering pipe is slidably arranged between the proximal end of the first insulating tube and the distal end of the second insulating tube in the pipe inner hole.

11. An endoscope comprising:
 an insertion portion including a distal end portion, a bending portion and a flexible tube portion continuously provided in this order from a distal end side; and
 an image pickup optical portion and a moving mechanism portion arranged in the distal end portion,
 wherein the image pickup optical portion includes:
  an image pickup device unit including an image pickup device, and
  a lens unit including a moving lens that moves to a first observation position and a second observation position, the lens unit being included in an optical system that forms an optical image on an image pickup surface of the image pickup device,
 wherein the moving mechanism portion is an actuator apparatus and includes,
  a first moving mechanism portion including a first elastic member having an urging force to cause a moving lens frame in which the moving lens in the lens unit is disposed to be arranged at the first observation position,
  a second moving mechanism portion including a second elastic member having an urging force larger than the urging force of the first elastic member, the urging force making the moving lens frame be arranged at the second observation position, and a shape memory alloy wire having a property of extending/contracting as a result of a temperature thereof changing due to a current applied from an external power supply via an electric cable, the shape memory alloy wire holding the second elastic member in a tensionless state when the shape memory alloy wire is extended, and contracting the second elastic member into a predetermined state and holding the second elastic member when the shape memory alloy wire is contracted, the shape memory alloy wire having a distal end portion and a proximal end portion arranged in the flexible tube portion of the insertion portion, the distal end portion being positioned on the bending portion side in the flexible tube portion;
 wherein the second moving mechanism portion further includes a driving force transmitting wire having a distal end portion and a proximal end portion, the distal end portion being fixed to the moving lens frame, the proximal end portion being fixed to the distal end portion of the shape memory alloy wire, wherein a fixing portion of the distal end portion of the shape memory alloy wire and the proximal end portion of the driving force transmitting wire is positioned in the flexible tube portion of the insertion portion;

wherein the driving force transmitting wire is pulled with contraction of the shape memory alloy wire to cause the contact member fixed to the distal end portion of the driving force transmitting wire to move against the urging force of the second elastic member and cancel the urging force from the second elastic member to the moving frame projection portion.

* * * * *